(12) United States Patent
El-Tayar et al.

(10) Patent No.: US 6,914,121 B2
(45) Date of Patent: Jul. 5, 2005

(54) PEG-LHRH ANALOG CONJUGATES

(75) Inventors: Nabil El-Tayar, Milton, MA (US); Xuan Zhao, Huntsville, AL (US); Michael D. Bentley, Huntsville, AL (US)

(73) Assignee: Applied Research Systems Ars Holding N.V., Curacao (NL)

( * ) Notice: Subject to any disclaimer, the term of this patent is extended or adjusted under 35 U.S.C. 154(b) by 0 days.

(21) Appl. No.: 10/184,126

(22) Filed: Jun. 28, 2002

(65) Prior Publication Data

US 2002/0183257 A1 Dec. 5, 2002

Related U.S. Application Data

(62) Division of application No. 09/698,134, filed as application No. PCT/US99/09160 on Apr. 28, 1999, now Pat. No. 6,433,135.
(60) Provisional application No. 60/083,340, filed on Apr. 28, 1998.

(51) Int. Cl.$^7$ .................. A61K 38/24; C07K 17/00; C07K 7/00
(52) U.S. Cl. .............. 530/313; 530/328; 530/334; 530/338; 530/344; 424/9.1; 424/185.1; 514/2; 514/506
(58) Field of Search ............................. 530/313, 328, 530/334, 338, 344; 424/9.1, 185.1; 514/2, 506

(56) References Cited

U.S. PATENT DOCUMENTS 5,840,900 A  11/1998  Greenwald et al.

FOREIGN PATENT DOCUMENTS

| EP | 0 377 585 B1 | 7/1995 |
| EP | 0 377 665 B1 | 7/1995 |
| WO | 94/04193 | 3/1994 |
| WO | 94/27641 | 12/1994 |
| WO | 96/21469 | 7/1996 |
| WO | 96/21489 | 7/1998 |

OTHER PUBLICATIONS

Emons G. et al., Recent Results cancer Res. 124, 55–68 (1992).*
El-Roeiy A. et al., Curr. Opin. Obstet. Gynecol. 2 (2) 166–172 (1990).*
Karten M. J. et al., Endocrine Reviews vol. 7, No. 1, 44–66 1986).
Nicholson R. I. et al., Cancer Treat. Res. 39, 1–23 (1988).
Kolb V. M. Prog. Drug. Res. 42, 39–52 (1992).
Klijn J.G.M., Recent Results cancer Res. 124, 75–90 (1992).
Felix et al., "Site–Specific Poly(ethylene glycol)ylation of Peptides", American Chemical Society, 218–238 (1997).
XP–002114783 ABSTRACT—"Peptide(s) modified with polyethylene glycol—e.g. calcitonin GRP, elastase, etc. have prolonged activity" Jun. 25, (1991), for JP 03148298 by Sano et al.
XP–002068523 Zalipsky—"Functionalized Poly(ethylene glycol) for Preparation of Biologically Relevant Conjugates", Bioconjugate Chem., 6:150–165 (1995).
Felix et al., "Site–Specific Poly(ethylene glycol)ylation of Peptides", American Chemical Society, 218–238 (1997).
XP–002114783 ABSTRAST—"Peptide(s) modified with polyethylene glycol—e.g. calcitonin GRP, elastase, etc. *have prolonged activity*" (1991).
XP–002068523 Zalipsky—"Functionalized Poly(ethylene glycol) for Preparation of Biologically Relevant Conjugates", Bioconjugate Chem., 6:150–165 (1995).

* cited by examiner

Primary Examiner—Jon Weber
Assistant Examiner—Chih-Min Kam
(74) Attorney, Agent, or Firm—Browdy and Neimark

(57) ABSTRACT

PEG-LHRH analog conjugates, where a PEG moiety is covalently bound to a serine residue of a LHRH analog either directly or via a bifunctional linker molecule, such as an amino acid, and methods for producing these conjugates are provided in the present invention. Also provided are a pharmaceutical composition and a method for treating pathologies in which LHRH analog administration is beneficial.

13 Claims, 2 Drawing Sheets

HYDROLYSIS OF mPEG-ANTIDE AT 37°C AND pH 7.2
( R = 0.996, t1/2 = 5.56 HOURS )

PEG-LHRH ANALOG CONJUGATES

CROSS REFERENCE TO RELATED APPLICATION

This application is a divisional of U.S. Application Ser. No. 09/698,134, filed Oct. 30, 2000, now U.S. Pat. No. 6,433,135, which a continuation of International PCT application PCT/US99/09160, designating the United States, filed Apr. 28, 1999, and claims the benefit of provisional application Ser. No. 60/083,340, filed Apr. 28, 1998, the entire contents of the above applications are hereby incorporated herein by reference.

FIELD OF THE INVENTION

The present invention relates to PEG-LHRH analog conjugates wherein the PEG unit is covalently bound to Ser[4] either directly or via a bifunctional linker molecule, such as an amino acid. The process for their production as well as their use in the therapy, prognosis or diagnosis of the diseases, in which LHRH analogs' administration is advisable, are further objects of the present invention.

BACKGROUND OF THE INVENTION

Covalent attachment of the hydrophilic polymer polyethylene glycol, (PEG), also known as polyethylene oxide, (PEO), to molecules has important applications in biotechnology and medicine. In its most common form, PEG is a linear polymer having hydroxyl groups at each terminus:

$$HO-CH_2-CH_2O\ (CH_2CH_2O)_n CH_2CH_2-OH$$

This formula can be represented in brief as HO-PEG-OH, where it is meant that -PEG-represents the polymer backbone without the terminal groups:

"-PEG-" means "$-CH_2CH_2O(CH_2CH_2O)_n CH_2CH_2-$"

PEG is commonly used as methoxy-PEG-OH, (m-PEG), in which one terminus is the relatively inert methoxy group, while the other terminus is a hydroxyl group that is subject to chemical modification.

$$CH_3O-(CH_2CH_2O)_n-CH_2CH_2-OH.$$

Branched PEGs are also in common use. The branched PEGs can be represented as $R(-PEG-OH)_m$ in which R represents a central core moiety such as pentaerythritol or glycerol, and m represents the number of branching arms. The number of branching arms (m) can range from three to a hundred or more. The hydroxyl groups are subject to chemical modification.

Another branched form, such as that described in PCT patent application WO 96/21469, has a single terminus that is subject to chemical modification. This type of PEG can be represented as $(CH_3O-PEG-)_p R-X$, whereby p equals 2 or 3, R represents a central core such as lysine or glycerol, and X represents a functional group such as carboxyl that is subject to chemical activation. Yet another branched form, the "pendant PEG", has reactive groups, such as carboxyl, along the PEG backbone rather than at the end of PEG chains.

In addition to these forms of PEG, the polymer can also be prepared with weak or degradable linkages in the backbone. For example, Harris has shown in U.S. patent application Ser. No. 06/026,716 that PEG can be prepared with ester linkages in the polymer backbone that are subject to hydrolysis. This hydrolysis results in cleavage of the polymer into fragments of lower molecular weight, according to the above reaction scheme:

$$-PEG-CO_2-PEG-+H_2O \rightarrow -PEG-CO_2H+HO-PEG-$$

As used herein, the term polyethylene glycol or PEG is meant to include all the above described derivatives.

The copolymers of ethylene oxide and propylene oxide are closely related to PEG in their chemistry, and they can be used instead of PEG in many of its applications. They have the following general formula:

$$HO-CH_2CHRO\ (CH_2CHRO)_n CH_2CHR-OH$$

wherein R is H or $CH_3$.

PEG is a useful polymer having the property of high water solubility as well as high solubility in many organic solvents. PEG is also non-toxic and non-immunogenic. When PEG is chemically attached (PEGylation) to a water insoluble compound, the resulting conjugate generally is water soluble as well as soluble in many organic solvents.

Luteinizing hormone releasing hormone (LHRH or GnRH) is a decapeptide secreted by the hypothalamus and capable of inducing the release of both LH and FSH. It has the following formula: pyroGlu-His-Trp-Ser-Tyr-Gly-Leu-Arg-Pro-Gly-$NH_2$ (SEQ ID NO:1).

LHRH can either stimulate pituitary gonadotropin secretion or be a potent inhibitor. When administered in a precise pulsatile pattern, LHRH can restore the normal cyclic gonadotropin secretion. Pulsatile administration of LHRH using a computerized pump was used with good results in the induction of ovulation in anovulatory women with hypothalamic dysfunction. When administered chronically, LHRH or its agonists proved to be potent inhibitors of gonadotropic secretion, providing a temporary (fully reversible) gonadotropin specific medical hypophisectomy.

To date, thousands of LHRH analogs have been synthesized that can act either as agonists or antagonists. In order to produce LHRH antagonists, which work by receptor occupancy, it is necessary to substitute several amino acids on the LHRH molecule. Antagonists also require precise topological features to achieve high binding affinity to the receptor. There are many recently synthesized LHRH analogs in which the amino acids contain aromatic or other functional groups capable of the so-called hydrotropic interaction. The use of LHRH antagonists with their immediate inhibition of gonadotrophin release may be useful in therapeutic areas, such as contraception and in treatment of hormone-dependent disorders. In the case of hormone-dependent tumors, avoiding the initial stimulatory phase produced by LHRH agonists may be a particular advantage. For a review on LHRH analogs, see Karten and Rivier, 1986.

Antide, in particular, is a potent LHRH antagonist, with formula, biological activity and preparation as described in EP Patent 377,665 and reported here below.

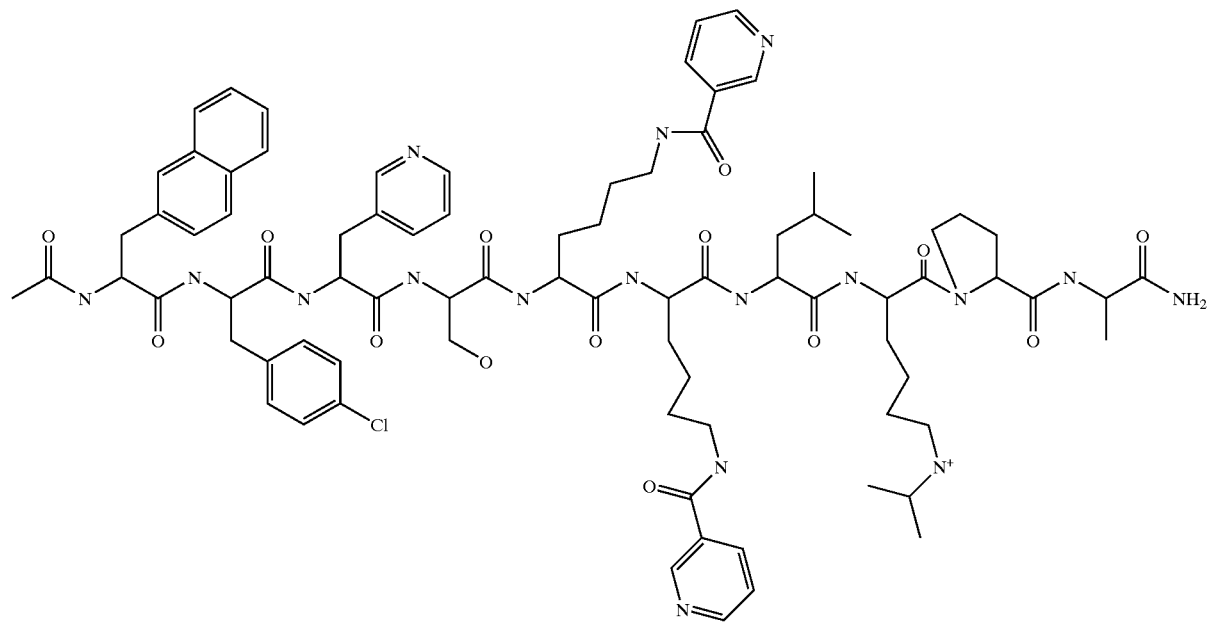

Antide

[Acetyl-D-3-(2'-Naphthyl)-alanine)[1], D-(4-Chlorophenyl)-alanine[2], D-3-(3'-Pyridyl)-alanine[3], Lysine (NE-Nicotinoyl)[5], D-Lysine(NE-Nicotinoyl)[6], Lysine (NE-Isopropyl)[8], D-Alanine[10]]-Gonadotropin Releasing Hormone (GnRH)

From studies carried out by the present inventors, it was found, for example, that antide has a very poor solubility in 0.9% NaCl solution (solubility 25 µg/ml) or other isotonic media such as phosphate buffered saline (solubility was 16 µg/ml). Previous formulations of antide (e.g., antide 1 mg/ml in 5% glucose) have shown poor bioavailability and pharmacokinetic reproducibility.

Covalent attachment of PEG to peptides is a potentially useful approach for delivering water insoluble peptide drugs as shown by Felix (A. M. Felix in J. M. Harris and S. Zalipsky, Eds., Poly(ethylene glycol) Chemistry and Biological Applications, A.C.S Symposium Series 680, pp 218–238, A.C.S. Washington, DC, 1997).

JP patent application JP 3148298 describes peptides—(e.g., including GnRH) PEG conjugates obtained by reacting the guanidino group, present for example in the arginine residue, with PEG, while protecting the amino groups present in the molecules.

Citation of any document herein is not intended as an admission that such document is pertinent prior art, or considered material to the patentability of any claim of the present application. Any statement as to content or a date of any document is based on the information available to applicants at the time of filing and does not constitute an admission as to the correctness of such a statement.

SUMMARY OF THE INVENTION

This invention provides novel PEG-LHRH analogs conjugates wherein a PEG unit is covalently bound to Ser[4] either directly or via a bifunctional linker molecule, such as an amino acid. PEG or PEG-linker molecule is bonded, specifically, to the alcohol function of the serine residue. The linkage between the LHRH analog and the polyethylene glycol or the PEG-linker molecule in these conjugates is subject to hydrolysis at physiological pH (7.2–7.4) and is preferably also subject to hydrolysis by esterases present in the blood.

DETAILED DESCRIPTION OF THE INVENTION

Figure 1:
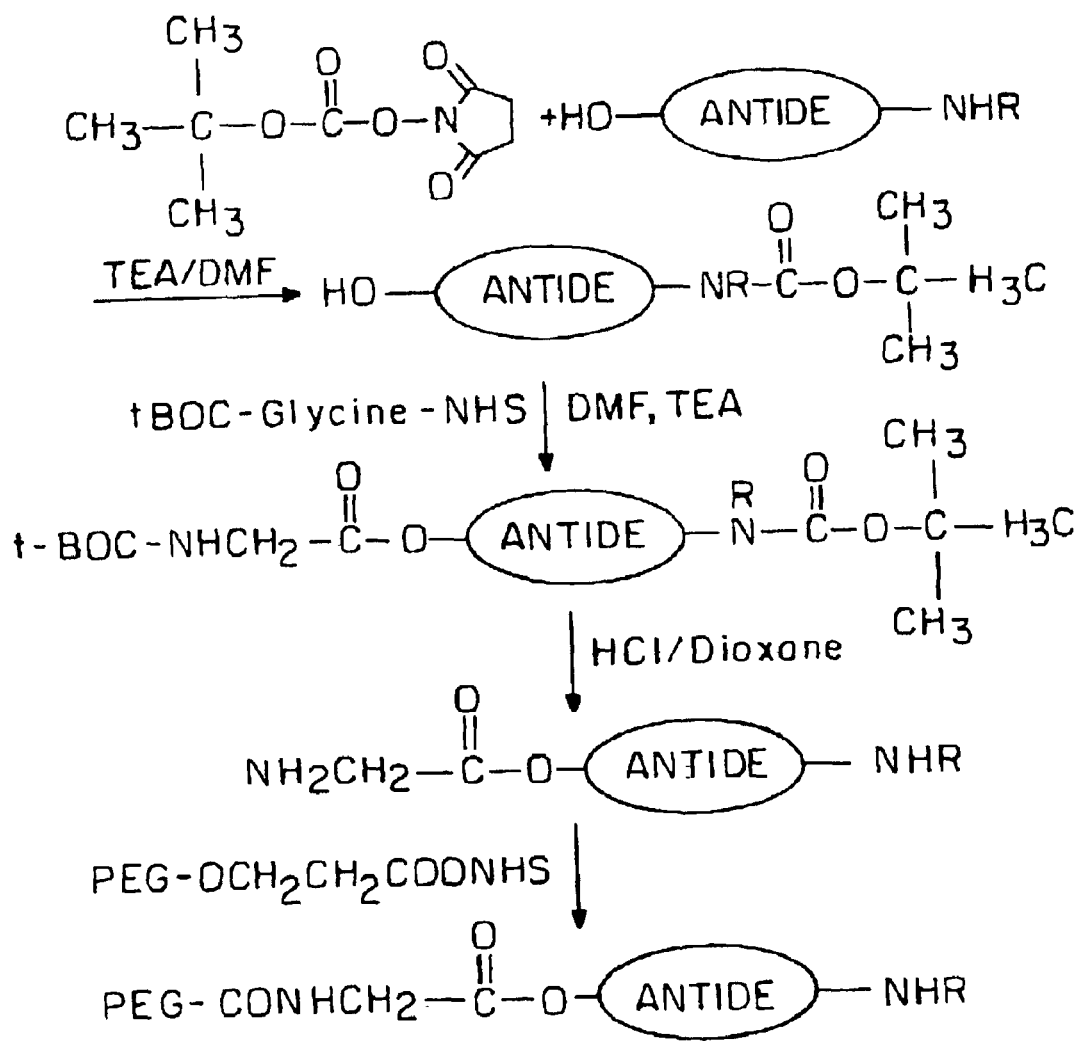
FIG. 1 shows a reaction scheme for preparing a PEG-antide conjugate with a glycine linker inserted between the PEG and the antide moieties.

The conjugates of the present invention, preferably, show a solubility in water of at least 30 mg/ml at room temperature and physiological pH (7.2–7.4) and a solubility in a physiological saline solution of at least 10 mg/ml at the same conditions.

In the case in which the LHRH analog is antide, for example, such properties enable the use of antide as a drug whereas, previously, development of antide as a drug has been rendered difficult due to its poor water solubility.

The term "LHRH-analogs", as used herein, is meant to include any decapeptide which is an LHRH agonist or antagonist. Preferably the LHRH analog is an LHRH antagonist; more preferably it is antide.

The conjugates of the present invention can be prepared by any of the methods known in the art. According to an embodiment of the invention, the LHRH analog is reacted with a PEGylating agent in a suitable solvent and the desired conjugate is isolated and purified, for example, by applying one or more chromatographic methods.

"Chromatographic methods" means any technique that is used to separate the components of a mixture by their application on a support (stationary phase) through which a solvent (mobile phase) flows. The separation principles of the chromatography are based on the different physical nature of stationary and mobile phase.

Some particular types of chromatographic methods, which are well-known in the literature, include: liquid, high pressure liquid, ion exchange, absorption, affinity, partition, hydrophobic, reversed phase, gel filtration, ultrafiltration or thin-layer chromatography.

The "PEGylating agent" as used in the present application means any PEG derivative, which is capable of reacting with the OH of a serine residue or a functional group of a bifunctional linker molecule, such as the amino group of an amino acid linker molecule. The other functional group of the linker molecule serves to form a covalent linkage to the serine residue of a LHRH analog, i.e., the carboxyl group of an amino acid linker molecule forms an ester linkage with serine. It can be an alkylating reagent, such as PEG aldehyde, PEG epoxide or PEG tresylate, or it can be an acylating reagent, such as PEG-O—$(CH_2)_nCO_2$-Z where n=1–3 and Z is N-succinimidyl or other suitable activating group.

The PEGylating agent is used in its mono-methoxylated form where only one terminus is available for conjugation, or in a bifunctional form where both termini are available for conjugation, such as for example in forming a conjugate with two LHRH analogs covalently attached to a single PEG moiety. It has a molecular weight between 500 and 100,000, preferably between about 5,000 and 40,000 (40 kDa) and more preferably between about 10 kDa and 40 kDa and most preferably between about 20 kDa and 40 kDa.

If the PEGylating agent is an acylating agent, it can contain either a norleucine or ornithine residue bound to the PEG unit via an amide linkage. These residues allow a precise determination of the linked PEG units per mole of peptide (see for example Sartore et al., 1991).

A solvent for the PEGylation reaction is preferably a polar aprotic solvent, such as DMF, DMSO, pyridine, etc.

When the LHRH analog is reacted with the PEGylating agent, derivatization can occur on the OH of the $Ser^4$ moiety, as well as on the amine nitrogen of other residues, such as, for example, on the ε-amino group of lysine (in case of antide, on N-Isopropyl-$Lys^8$). In such reactions, high selectivity for amine PEGylation can occur. Products formed by PEGylation on amines are amides and while PEG amides can be water soluble, the amide linkage can be stable under physiological conditions, and thus the LHRH analog could not be substantially hydrolytically released in vivo. Therefore, using this method, the PEG-LHRH analog ester should be separated from the PEG-LHRH analog amide using chromatography. A limitation of this method is, therefore, low yield of the desired PEG-LHRH analog conjugate.

Therefore, in a preferred embodiment, the LHRH analog is protected on the amine groups which could either react with the PEGylating agent or with a bifunctional linker molecule prior to PEGylation.

In the case of antide, it is therefore preferable to reversibly protect the N-Isopropyl-$Lys^8$ residue with a group that can be removed using photochemical, mild hydrolytic, or hydrogenation methods. With the nitrogen thus protected, the hydroxyl group on the serine residue is reacted with a PEGylating reagent to form a PEG ester and the protecting group on the N-Isopropyl-$Lys^8$ is then removed to yield antide selectively PEGylated on the hydroxyl of the serine residue by an ester linkage. The conditions for removal of the amine protecting group must be sufficiently mild to avoid cleavage of the PEG-antide ester linkage. In another embodiment where a bifunctional linker or spacer molecule is used to link a PEG moiety to an LHRH analog such as antide, the protecting group is preferably removed after a bifunctional linker molecule is covalently bound to the serine residue of an LHRH analog or can be removed after PEGylation of the bifunctional linker molecule covalently bound to the LHRH analog.

Preferred reagents for protection include benzyloxycarbonyl chloride or ring-substituted derivatives of this compound, N-hydroxysuccinimidyl or 1-benzotriazolyl esters of benzyloxycarbonic acid or ring substituted derivatives of t-butoxycarbonyl chloride or the N-hydroxysuccinimidyl or 1-benzotriazolyl esters of t-butoxycarbonic acid.

In another embodiment of the invention, the conjugates of the invention can be prepared by using an appropriate PEGylated serine such as Fmoc-Ser(PEG)-OH or tBoc-Ser(PEG)-OH instead of serine during the solid-phase synthesis of the LHRH analogs. An example of Fmoc-Ser(PEG)-OH derivative is shown below.

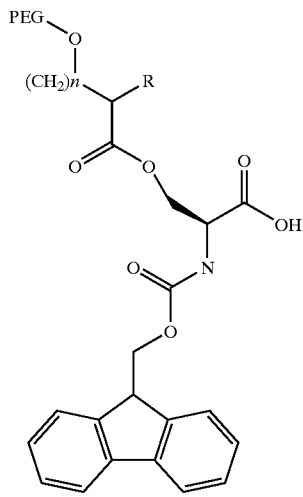

Fmoc-Ser(PEG)-OH

A regulation of the rate of release in vivo of the LHRH analog can be accomplished by varying n and R in the PEG linkage. In general, as n increases, the rate of release of the LHRH analog decreases and if R is alkyl, the rate of release of the LHRH analog is lower than the rate of release if R is H. In general, as the size of R increases, the rate of release of the LHRH analog, or antide in particular, decreases. Variation of n and R thus provides substantially precise control of the delivery rate in vivo of antide when used as a drug.

According to recent studies, such as U.S. Pat. No. 5,840,900, higher molecular weight PEG appear to be important for obtaining therapeutic efficacy in certain cases. For antide, three PEG-antide conjugates with PEGylating agents having molecular weights of 20 kDa or 40 kDa have been prepared by modifying the protection-deprotection procedure. In a preferred embodiment, the PEGylation rate of antide, particularly with higher molecular weight PEG moieties, is increased by first attaching a linker molecule, such as glycine, to the antide and then PEGylating the linker molecule covalently attached to the antide. The reaction scheme for preparing a PEGylated antide with a glycine linker is shown in FIG. 1. The scheme in FIG. 1 can be used for preparing, for example, conjugates such as PEG2-glycine-antide 20 k (a branched 20 kDa PEG can be used), mPEG-glycine-antide (a linear 20 kDa mPEG can be used), and PEG2-glycine-antide 40 k (a branched 40 kDa PEG can be used). It will be appreciated by those of skill in the art that the scheme shown in FIG. 1 is not limited to antide or glycine linker but can be applied to other LHRH analogs and linker molecules.

The linker molecule is preferably a small bifunctional molecule, which can rapidly react with the OH group on a serine residue of a LHRH analog. This linker molecule is preferably a heterobifunctional linker molecule, such as an amino acid, which forms an ester with a serine residue of a LHRH analog. The second functional group of the linker molecule serve as the site for PEGylation by the PEGylating agent. The amino acid, glycine, is a preferred heterobifunctional linker molecule according to the present invention. Other suitable linker molecules can be readily recognized or determined by those of skill in the art.

Another object of the present invention is to provide the conjugates in substantially purified form in order for them to be suitable for use in pharmaceutical compositions, as active ingredient for the treatment, diagnosis or prognosis of pathologies in which LHRH analogs administration is advisable. Such pharmaceutical compositions represent a further object of the present invention.

If the LHRH analog is antide, the above-mentioned pathologies include endometriosis, uterine fibroids, hormonal-dependent cancers (prostate, breast), uterine myoma, LH surge in women undergoing in-vitro fertilization and all the other pathological states reported in EP 377,665.

Further embodiments and advantages of the invention will be evident in the following description.

An embodiment of the invention is the administration of a pharmacologically active amount of the conjugates of the invention to subjects at risk of developing one of the diseases reported above or to subjects already showing such pathologies.

Any route of administration compatible with the active principle can be used. The preferred is parenteral administration, such as subcutaneous, intramuscular or intravenous injection. The dose of the active ingredient to be administered depends on the basis of the medical prescriptions according to age, weight and the individual response of the patient.

The daily non-weighted dosage for the patient can be between 0.2 to 20 mg, and the preferable daily dose is between 0.2 to 10 mg.

The pharmaceutical composition for parenteral administration can be prepared in an injectable form comprising the active principle and a suitable vehicle. Vehicles for the parenteral administration are well known in the art and comprise, for example, water, saline solution, Ringer solution and/or dextrose.

The vehicle can contain small amounts of excipients in order to maintain the stability and isotonicity of the pharmaceutical preparation.

The preparation of the cited solutions can be carried out according to the ordinary modalities.

The present invention has been described with reference to the specific embodiments, but the content of the description comprises all modifications and substitutions which can be brought by a person skilled in the art without extending beyond the meaning and purpose of the claims.

The invention will now be described by means of the following Examples, which should not be construed as in any way limiting the present invention.

EXAMPLE 1

Preparation of PEG-antide Conjugate

Antide (10 mg, 6.3 mmole) was dissolved in 15 ml of anhydrous pyridine and the resulting solution was azeotropically distilled under vacuum at 45° C. until about 8 ml of pyridine remained. After cooling the solution to room temperature, the succinimidyl ester of carboxymethylated mPEG (93 mg, 19 mmole, Shearwater Polymers, Huntsville, Ala.) was added and the solution was stirred for 48 hours under nitrogen at room temperature.

The pyridine was then removed under vacuum and products were collected by vacuum filtration after precipitation in ether (50 ml), and dried in vacuo.

The product (50 mg) obtained from the previous step was dissolved in deionized water (1.5 ml), and the mixture was filtered through a 0.2 ml syringe filter. The solution was loaded onto an ion exchange chromatography column (CM Sepharose Fast Flow, Pharmacia, Uppsala, Sweden). Eluents were deionized water and 50 mM NaCl solution with a gradient from zero to 60% salt solution. Three peaks were observed, with the middle peak being the desired PEG-antide conjugate, in which the PEG chain is bound to $Ser^4$.

This conjugate was collected by fractionation and freeze-dried. The product was shown to be highly water soluble (>30 mg/ml).

Hydrolysis Kinetics of the PEG-antide Conjugate

Figure 2:
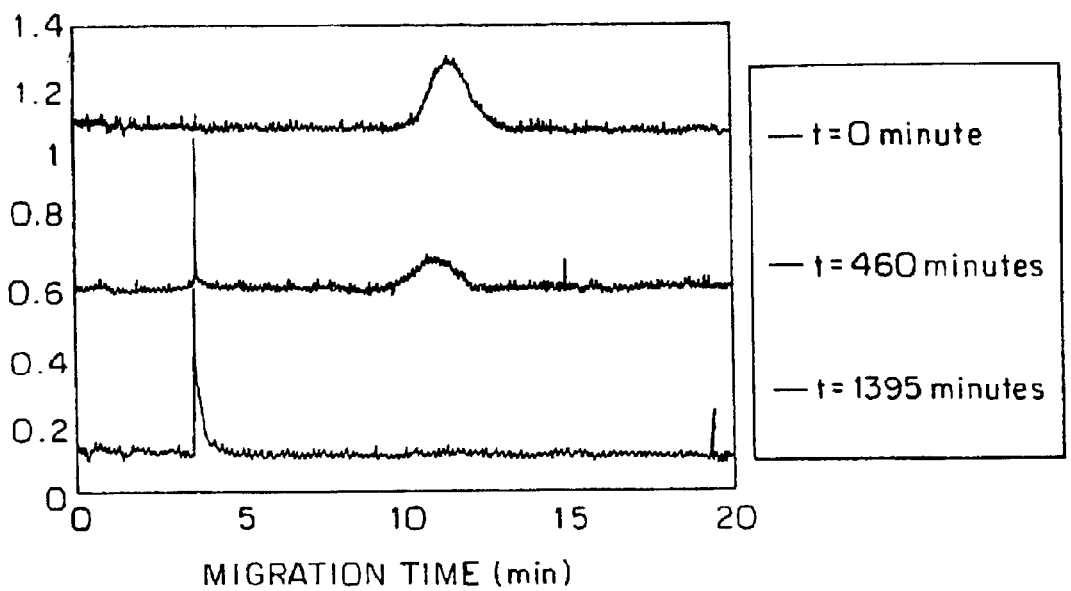
FIG. 2 shows the Capillary Electrophoresis (CE) graphs of hydrolysis of the PEG-antide conjugate at 37° C. in phosphate buffer pH 7.2 at t=0, 460 and 1395 minutes.
Figure 3:
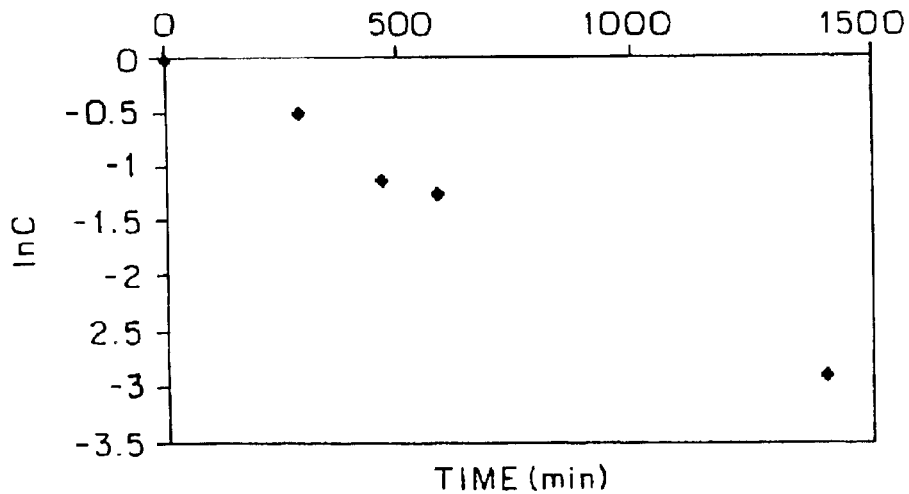
FIG. 3 shows the hydrolysis kinetics plot deduced from the data of FIG. 2 assuming a pseudo first-order kinetics.

The hydrolysis of the conjugate was determined using capillary electrophoresis (CE). The calculated half life under these conditions is 5.5 hours as illustrated in FIGS. 2 and 3.

Having now fully described this invention, it will be appreciated that by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed:

1. A method for treating a pathology selected from the group consisting of a hormonal dependent cancer, endometriosis, uterine fibroids, uterine myoma, and luteinizing hormone (LH) surge in woman undergoing in vitro fertilization, comprising administering to a subject in need thereof an effective amount of a conjugate having a polyethylene glycol (PEG) moiety covalently bound to the serine residue of antide to treat said pathology, wherein said conjugate is capable of hydrolysis to release antide.

2. The method according to claim 1, wherein said PEG moiety is covalently bound to said serine residue of antide via a bifunctional linker molecule.

3. The method according to claim 2, wherein said bifunctional linker molecule is a heterobifunctional linker molecule.

4. The method according to claim 3, wherein said bifunctional linker molecule forms an ester with said serine residue of antide.

5. The method according to claim 3, wherein said heterobifunctional linker molecule is an amino acid.

6. The method according to claim 5, wherein said heterobifunctional linker molecule is glycine.

7. The method according to claim 1, wherein said pathology is a hormonal dependent cancer.

8. The method according to claim 7, wherein said hormonal dependent cancer is breast cancer.

9. The method according to claim 7, wherein said hormonal dependent cancer is prostate cancer.

10. The method according to claim 1, wherein said pathology is endometriosis.

11. The method according to claim 1, wherein said pathology is uterine fibroids.

12. The method according to claim 1, wherein said pathology is uterine myoma.

13. The method according to claim 1, wherein said pathology is luteinizing hormone (LH) surge in women undergoing in vitro fertilization.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Glu is modified with a pyro group.
<220> FEATURE:
<221> NAME/KEY: misc_feature
<222> LOCATION: (10)..(10)
<223> OTHER INFORMATION: Gly is modified with -NH2 group.

<400> SEQUENCE: 1

Glu His Trp Ser Tyr Gly Leu Arg Pro Gly
1               5                   10
```